(12) United States Patent
McMillen

(10) Patent No.: US 9,442,614 B2
(45) Date of Patent: Sep. 13, 2016

(54) TWO-DIMENSIONAL SENSOR ARRAYS

(71) Applicant: BeBop Sensors, Inc., Berkeley, CA (US)

(72) Inventor: Keith A. McMillen, Berkeley, CA (US)

(73) Assignee: BeBop Sensors, Inc., Berkeley, CA (US)

(*) Notice: Subject to any disclaimer, the term of this patent is extended or adjusted under 35 U.S.C. 154(b) by 85 days.

(21) Appl. No.: 14/464,551

(22) Filed: Aug. 20, 2014

(65) Prior Publication Data

US 2015/0331523 A1    Nov. 19, 2015

Related U.S. Application Data

(63) Continuation-in-part of application No. 14/299,976, filed on Jun. 9, 2014.

(60) Provisional application No. 61/993,953, filed on May 15, 2014.

(51) Int. Cl.
| | |
|---|---|
| G06F 3/044 | (2006.01) |
| G06F 3/041 | (2006.01) |
| G06F 3/045 | (2006.01) |
| G06F 1/16 | (2006.01) |
| A43B 3/00 | (2006.01) |
| A61B 5/00 | (2006.01) |

(52) U.S. Cl.
CPC ............ *G06F 3/044* (2013.01); *A43B 3/0005* (2013.01); *A61B 5/6807* (2013.01); *G06F 1/16* (2013.01); *G06F 3/045* (2013.01); *G06F 3/0414* (2013.01); *G06F 3/0416* (2013.01); *G06F 3/0418* (2013.01); *G06F 2203/04102* (2013.01); *G06F 2203/04103* (2013.01); *G06F 2203/04104* (2013.01); *G06F 2203/04112* (2013.01)

(58) Field of Classification Search
None
See application file for complete search history.

(56) References Cited

U.S. PATENT DOCUMENTS

| | | |
|---|---|---|
| 4,294,014 A | 10/1981 | Baumann et al. |
| 4,852,443 A | 8/1989 | Duncan et al. |
| 5,128,880 A | 7/1992 | White |
| 5,131,306 A | 7/1992 | Yamamoto |
| 5,237,520 A | 8/1993 | White |
| 5,288,938 A | 2/1994 | Wheaton |
| 5,429,092 A | 7/1995 | Kamei |
| 5,659,395 A | 8/1997 | Brown et al. |
| 5,695,859 A * | 12/1997 | Burgess ............... H01H 1/029 200/85 R |
| 5,729,905 A | 3/1998 | Mathiasmeier et al. |
| 5,822,223 A | 10/1998 | Genest |
| 5,866,829 A | 2/1999 | Pecoraro |
| 5,878,359 A | 3/1999 | Takeda |

(Continued)

FOREIGN PATENT DOCUMENTS

| | | |
|---|---|---|
| CN | 200980381 Y | 11/2007 |
| CN | 201920728 U | 8/2011 |

(Continued)

OTHER PUBLICATIONS

U.S. Appl. No. 14/299,976, filed Jun. 9, 2014, McMillen.

(Continued)

*Primary Examiner* — Dismery Mercedes
(74) *Attorney, Agent, or Firm* — Weaver Austin Villeneuve & Sampson LLP

(57) ABSTRACT

Two-dimensional sensor arrays incorporating piezoresistive materials are described.

55 Claims, 7 Drawing Sheets

(56) References Cited

U.S. PATENT DOCUMENTS

| | | | |
|---|---|---|---|
| 5,943,044 A | 8/1999 | Martinelli et al. | |
| 5,989,700 A | 11/1999 | Krivopal | |
| 6,029,358 A | 2/2000 | Mathiasmeier et al. | |
| 6,155,120 A * | 12/2000 | Taylor | A61B 5/1036 73/862.046 |
| 6,215,055 B1 | 4/2001 | Saravis | |
| 6,216,545 B1 | 4/2001 | Taylor | |
| 6,331,893 B1 | 12/2001 | Brown et al. | |
| 6,964,205 B2 | 11/2005 | Papakostas et al. | |
| 7,157,640 B2 | 1/2007 | Baggs | |
| 7,332,670 B2 | 2/2008 | Fujiwara et al. | |
| 7,409,256 B2 | 8/2008 | Lin et al. | |
| 7,493,230 B2 | 2/2009 | Schwartz et al. | |
| 7,536,794 B2 | 5/2009 | Hay et al. | |
| 7,608,776 B2 | 10/2009 | Ludwig | |
| 7,719,007 B2 * | 5/2010 | Tompkins | G01L 1/142 257/48 |
| 7,754,956 B2 | 7/2010 | Gain et al. | |
| 7,855,718 B2 | 12/2010 | Westerman | |
| 7,928,312 B2 | 4/2011 | Sharma | |
| 8,117,922 B2 | 2/2012 | Xia et al. | |
| 8,274,485 B2 * | 9/2012 | Liu | G06F 3/0416 178/18.01 |
| 8,448,530 B2 * | 5/2013 | Leuenberger | A61J 1/035 73/760 |
| 8,479,585 B2 | 7/2013 | Shaw-Klein | |
| 8,680,390 B2 | 3/2014 | McMillen et al. | |
| 9,038,482 B2 | 5/2015 | Xia et al. | |
| 9,075,404 B2 | 7/2015 | McMillen et al. | |
| 9,076,419 B2 | 7/2015 | McMillen et al. | |
| 2004/0093746 A1 | 5/2004 | Varsallona | |
| 2007/0234888 A1 | 10/2007 | de Moraes | |
| 2008/0158145 A1 | 7/2008 | Westerman | |
| 2008/0254824 A1 | 10/2008 | de Moraes | |
| 2009/0049980 A1 | 2/2009 | Sharma | |
| 2009/0237374 A1 * | 9/2009 | Li | G06F 3/0414 345/174 |
| 2009/0272197 A1 | 11/2009 | Ridao Granado et al. | |
| 2010/0149108 A1 * | 6/2010 | Hotelling | G06F 3/044 345/173 |
| 2010/0286951 A1 | 11/2010 | Danenberg et al. | |
| 2010/0315337 A1 | 12/2010 | Ferren et al. | |
| 2011/0088535 A1 | 4/2011 | Zarimis | |
| 2011/0088536 A1 | 4/2011 | McMillen et al. | |
| 2012/0026124 A1 * | 2/2012 | Li | G06F 3/0414 345/174 |
| 2012/0143092 A1 | 6/2012 | Xia et al. | |
| 2012/0191554 A1 | 7/2012 | Xia et al. | |
| 2012/0197161 A1 | 8/2012 | Xia et al. | |
| 2012/0198949 A1 | 8/2012 | Xia et al. | |
| 2013/0009905 A1 * | 1/2013 | Castillo | G06F 3/044 345/174 |
| 2013/0082970 A1 * | 4/2013 | Frey | G06F 3/0414 345/173 |
| 2013/0113057 A1 | 5/2013 | Taylor | |
| 2013/0239787 A1 | 9/2013 | McMillen et al. | |
| 2013/0275057 A1 * | 10/2013 | Perlin | G06F 3/0414 702/41 |
| 2013/0327560 A1 * | 12/2013 | Ichiki | G06F 3/044 174/133 R |
| 2014/0033829 A1 | 2/2014 | Xia et al. | |
| 2014/0107966 A1 | 4/2014 | Xia et al. | |
| 2014/0107967 A1 | 4/2014 | Xia et al. | |
| 2014/0107968 A1 | 4/2014 | Xia et al. | |
| 2014/0182170 A1 | 7/2014 | Wawrousek et al. | |
| 2014/0195023 A1 | 7/2014 | Statham et al. | |
| 2014/0222243 A1 | 8/2014 | McMillen et al. | |
| 2015/0084873 A1 * | 3/2015 | Hagenbuch | G06F 3/0416 345/173 |
| 2015/0261372 A1 | 9/2015 | McMillen et al. | |
| 2015/0316434 A1 | 11/2015 | McMillen et al. | |
| 2015/0317964 A1 | 11/2015 | McMillen et al. | |
| 2015/0331512 A1 | 11/2015 | McMillen et al. | |
| 2015/0331522 A1 | 11/2015 | McMillen et al. | |
| 2015/0331524 A1 | 11/2015 | McMillen et al. | |
| 2015/0331533 A1 | 11/2015 | McMillen et al. | |

FOREIGN PATENT DOCUMENTS

| | | |
|---|---|---|
| CN | 102551728 A | 7/2012 |
| CN | 202396601 U | 8/2012 |
| CN | 203234132 U | 10/2013 |
| CN | 102406280 B | 3/2014 |
| DE | 11 2010 004 038 T5 | 9/2012 |
| EP | 0 014 022 B1 | 11/1984 |
| EP | 2 682 724 A1 | 1/2014 |
| JP | H08-194481 | 7/1996 |
| JP | 2000-267664 A | 9/2000 |
| JP | 2008-515008 A | 5/2008 |
| KR | 10-2007-0008500 A | 1/2007 |
| KR | 100865148 B1 | 10/2008 |
| KR | 10-2014-0071693 A | 6/2014 |
| NL | 8900820 A | 11/1990 |
| WO | WO 99/20179 A1 | 4/1999 |
| WO | WO 2007/024875 A2 | 3/2007 |
| WO | WO 2011/047171 | 4/2011 |
| WO | WO 2015/175317 A1 | 11/2015 |

OTHER PUBLICATIONS

U.S. Office Action dated Sep. 12, 2012 issued in U.S. Appl. No. 12/904,657.

U.S. Office Action dated Apr. 15, 2013 issued in U.S. Appl. No. 12/904,657.

U.S. Notice of Allowance dated Nov. 8, 2013 issued in U.S. Appl. No. 12/904,657.

U.S. Office Action dated Mar. 12, 2015 issued in U.S. Appl. No. 14/173,617.

PCT International Search Report dated May 27, 2011, issued in PCT/US2010/052701.

PCT International Preliminary Report on Patentability and Written Opinion dated Apr. 26, 2012, issued in PCT/US2010/052701.

Japanese Office Action dated Feb. 25, 2014 issued in JP 2012-534361.

Roh, Jung-Sim et al. (2011) "Robust and reliable fabric and piezoresistive multitouch sensing surfaces for musical controllers," from Alexander Refsum Jensenius, Recorded at: *11th International Conference on New Interfaces for Musical Expression* May 30-Jun. 1, 2011, Oslo, Norway, a vimeo download at http://vimeo.com/26906580.

U.S. Notice of Allowance dated May 1, 2015 issued in U.S. Appl. No. 14/173,617.

U.S. Office Action dated Apr. 2, 2015 issued in U.S. Appl. No. 13/799,304.

U.S. Notice of Allowance dated Apr. 24, 2015 issued in U.S. Appl. No. 13/799,304.

U.S. Office Action dated Sep. 1, 2015 issued in U.S. Appl. No. 14/728,872.

PCT International Search Report and Written Opinion dated Sep. 3, 2015 issued in PCT/US2015/029732.

"Electronic Foot Size Measuring Devices," *Sensatech Research LTD., Custom Electronic Sensing Solutions*, Registered Office: 4 Heath Square, Boltro Road, Haywards Heath, RH16 1BL Company Registration No. 4524018 Cardiff [retrieved at http:www.electronicsarena.co.uk/companies/sensatech-research/products/electronic-foot-size-measureing-devices on Sep. 17, 2015], 3 pages.

"iStep® Digital Foot Scan," ( © 2002-2015) [retrieved at http://www.foot.com/site/iStep on Sep. 17, 2015], 1 page.

"Podotech Elftman," and Podotech Elftman Brochure (UK Version) [retrieved at http://www.podotech.com/diagnostics/podotech-elftman-2/ on Sep. 17, 2015] podo+tech®, Foot Care Technology Solutions, 7 pages.

"The Emed® -Systems," [retrieved at http://www.novel.de/novelcontent/emed on Sep. 17, 2015] novel.de, 4 pages.

* cited by examiner

TWO-DIMENSIONAL SENSOR ARRAYS

RELATED APPLICATION DATA

The present application is a continuation-in-part application and claims priority under 35 U.S.C. 120 to U.S. patent application Ser. No. 14/299,976 entitled Piezoresistive Sensors and applications filed on Jun. 9, 2014. The present application is also a non-provisional of and claims priority under 35 U.S.C. 119(e) to U.S. Provisional Patent Application No. 61/993,953 entitled Piezoresistive Sensors and Applications filed on May 15, 2014. The entire disclosures of both applications are incorporated herein by reference for all purposes.

BACKGROUND

Demand is rapidly rising for technologies that bridge the gap between the computing devices and the physical world. These interfaces typically require some form of sensor technology that translates information from the physical domain to the digital domain. The "Internet of Things" contemplates the use of sensors in a virtually limitless range of applications, for many of which conventional sensor technology is not well suited.

SUMMARY

According to a particular class of implementations, a sensor array includes a piezoresistive substrate. A first array of conductive traces is formed on the piezoresistive substrate and aligned with a first dimension of the sensor array. A second array of conductive traces is formed on the piezoresistive substrate and aligned with a second dimension of the sensor array. The sensor array has associated circuitry configured to apply drive signals to the first array of conductive traces, to receive detection signals from the second array of conductive traces, and to determine one or more locations of one or more corresponding touch events on a surface of the sensor array using the drive and detection signals.

According to some implementations, the piezoresistive substrate comprises a flexible piezoresistive material.

According to some implementations, the first and second arrays of conductive traces are formed on only one side of the piezoresistive substrate. According to other implementations, the first and second arrays of conductive traces are formed on both sides of the piezoresistive substrate.

According to some implementations, the conductive traces of the first array are substantially parallel to each other and oriented along the first dimension, and the conductive traces of the second array are substantially parallel to each other and oriented along the second dimension; the first and second dimensions being substantially perpendicular to each other.

According to some implementations, the conductive traces of the first array are characterized by a first conductivity, and the conductive traces of the second array are characterized by a second conductivity higher than the first conductivity. The circuitry is further configured to drive one end of a first conductive trace of the first array with a first signal, and to drive an opposing end of the first conductive trace with a second signal, and to receive a mixed signal from a second conductive trace of the second array. The mixed signal includes contributions from the first and second signals via the piezoresistive substrate, and the circuitry is configured to determine a first location of a first touch event along the first conductive trace with reference to a first value representing the contributions of the first and second signals to the mixed signal.

According to some implementations, the circuitry is further configured to determine one or more additional locations of one or more additional touch events along any of the conductive traces of the first array that are substantially simultaneous with the first touch event with reference to one or more additional values representing one or more additional mixed signals received from one or more of the conductive traces of the second array.

According to some implementations, the circuitry is further configured to determine the first location of the first touch event as being along the first conductive trace and between adjacent conductive traces of the second array. According to some implementations, the circuitry is configured to determine the first location of the first touch event with reference to an additional value representing an additional mixed signal received from an additional conductive trace of the second array.

According to some implementations, the circuitry is further configured to determine a second location of second touch event along the first conductive trace that is substantially simultaneous with the first touch event with reference to the first value and an additional value representing an additional mixed signal received from an additional conductive trace of the second array.

According to some implementations, the circuitry is further configured to drive one end of a third conductive trace of the first array with the first signal, and to drive an opposing end of the third conductive trace with a third signal. The mixed signal also includes additional contributions from the first signal and the third signal corresponding to a second touch event near the third conductive trace that is substantially simultaneous with the first touch event. The circuitry is further configured to generate the first value with reference to the additional contributions from the first and third signals corresponding to the second touch event.

According to some implementations, the circuitry is configured to resolve the first location of the first touch event to one of a plurality of discrete locations associated with the first conductive trace on the surface of the sensor array.

According to some implementations, the circuitry is further configured to determine a force value for each touch event representing a magnitude of a force for the corresponding touch event. According to some implementations, the circuitry is configured to determine the force value for each touch event with reference to an amplitude of a corresponding one of the detection signals.

According to some implementations, each of the conductive traces of the first array coincides with each of the conductive traces of the second array, and the circuitry is further configured to generate a data set for the sensor array with reference to the detection signals. The data set includes a data value for each coincidence of one of the conductive traces of the first array with one of the conductive traces of the second array. The circuitry is configured to determine the one or more locations of the one or more corresponding touch events with reference to the data set.

According to some implementations, the circuitry is further configured to determine a first location of a first touch event near a first coincidence of a first conductive trace of the first array and a second conductive trace of the second array by comparing the data value corresponding to the first coincidence to a threshold. According to some implementations, the threshold is determined with reference to an average of the data values.

According to some implementations, the circuitry is configured to repeat generation of the data set resulting in a plurality of data sets, each data set representing a state of the sensor array for a corresponding period of time. The circuitry is configured to determine the one or more locations of the one or more corresponding touch events with reference to the plurality of data sets. According to some implementations, the circuitry is configured to determine the one or more locations of the one or more corresponding touch events with reference to the plurality of data sets by comparing corresponding data values in successive ones of the data sets.

According to some implementations, the circuitry is configured to generate first and second data values for each coincidence of one of the conductive traces of the first array with one of the conductive traces of the second array. The first data value represents a location of any nearby touch event along the corresponding conductive trace of the first array, and the second data value represents a force associated with the nearby touch event.

According to some implementations, the circuitry is configured to determine a plurality of locations of a plurality of substantially simultaneous touch events on the surface of the sensor array using the drive and detection signals.

According to some implementations, the circuitry is configured to resolve detected touch events to a plurality of discrete locations on the surface of the sensor array.

According to some implementations, the array includes a plurality of force focusing elements each of which is aligned with one of the discrete locations. One or both of the form factor of the force focusing elements and the flexibility of the force focusing elements may be controlled to achieve a corresponding dynamic range of the sensor array. The force focusing elements may be part of the piezoresistive substrate. Alternatively, the array may include an additional substrate adjacent to a combination of the first and second arrays of conductive traces and the piezoresistive substrate. The force focusing elements may be formed on the additional substrate. According to some implementations, the force focusing elements are convex features on the additional substrate. According to some implementations, the additional substrate is part of an environmental protection enclosure for the combination of the first and second arrays of conductive traces and the piezoresistive substrate.

According to some implementations, a first additional substrate is adjacent to a combination of the first and second arrays of conductive traces and the piezoresistive substrate. The first additional substrate has a plurality of structural elements extending therefrom at least partially through the piezoresistive substrate in spaces between the conductive traces. The sensor array further includes a second additional substrate adjacent to the combination of the first and second arrays of conductive traces and the piezoresistive substrate on an opposite side of the combination from the first additional substrate. According to some implementations, the structural elements extend all of the way through the piezoresistive substrate and contact the second additional substrate without force exerted on the surface of the sensor array. According to some implementations, the structural elements extend only part of the way through the piezoresistive substrate. According to some implementations, the first and second additional substrates are part of an environmental protection enclosure for the combination of the first and second arrays of conductive traces and the piezoresistive substrate.

According to some implementations, the piezoresistive substrate includes a plurality of apertures, each of the apertures being aligned with a space between the conductive traces of the first and second arrays. According to some implementations, an additional substrate is adjacent to a combination of the first and second arrays of conductive traces and the piezoresistive substrate. The additional substrate has a plurality of structural elements extending therefrom at least partially through the apertures of the piezoresistive substrate. According to some implementations, the structural elements have a form factor corresponding to a shape of the apertures.

According to some implementations, the conductive traces of the first array are resistive traces, and the circuitry is configured to energize each of the conductive traces of the first array by simultaneously driving opposing ends of the conductive trace with first and second signals, respectively, using a plurality of signal busses. Each signal buss is connected to a plurality of the conductive traces of the first array. The opposing ends of each conductive trace of the first array are connected to a unique pair of the busses. According to some implementations, the conductive traces of the second array are characterized by substantially zero resistance, and at least some of the locations at which the circuitry is configured to determine touch events are along corresponding ones of the conductive traces of the first array and between respective pairs of the conductive traces of the second array.

According to some implementations, the circuitry is configured to resolve detected touch events to a plurality of discrete locations on the surface of the sensor array. The plurality of discrete locations form an array of Y discrete locations along the first dimension by X discrete locations along the second dimension. The first array of conductive traces includes X conductive traces, and the second array of conductive traces includes fewer than Y conductive traces. X and Y are integers greater than zero.

According to some implementations, the circuitry is configured to resolve detected touch events to a plurality of discrete locations on the surface of the sensor array. The plurality of discrete locations form an array of Y discrete locations along the first dimension by X discrete locations along the second dimension. The first array of conductive traces includes X conductive traces. X and Y are integers greater than zero. The sensor array further includes a plurality of busses by which the circuitry applies the drive signals to the first array of conductive traces, the plurality of busses including fewer than X busses.

According to some implementations, each of the conductive traces of the first array coincides with each of the conductive traces of the second array. The sensor array further includes a trace pattern at each coincidence of one of the conductive traces of the first array with one of the conductive traces of the second array. Each trace pattern includes a first trace extending from the corresponding conductive trace of the first array and a second trace extending from the corresponding conductive trace of the second array. The first and second traces have complementary shapes. According to some implementations, one or both of the shapes of the first and second traces and the distance between the first and second traces is controlled to achieve a corresponding dynamic range of the sensor array. According to a particular implementation, the complementary shapes of the first and second traces of each trace pattern are a clover shape and a cruciform shape.

According to another class of implementations, a sensor array includes a first array of conductive traces aligned with a first dimension of the sensor array, and a second array of conductive traces aligned with a second dimension of the sensor array. Piezoresistive material is configured to provide electrical connectivity between the conductive traces of the first and second arrays. The sensor array includes a plurality of force focusing elements each of which is aligned with one of a plurality of discrete locations on a surface of the sensor array. The sensor array has associated circuitry configured to apply drive signals to the first array of conductive traces, to receive detection signals from the second array of conductive traces, and to determine one or more locations of one or more corresponding touch events on the surface of the sensor array using the drive and detection signals. The circuitry is also configured to resolve detected touch events to corresponding ones of the plurality of discrete locations.

According to various implementations, one or both of the form factor of the force focusing elements and the flexibility of the force focusing elements is controlled to achieve a corresponding dynamic range of the sensor array. In some implementations, the force focusing elements are part of the piezoresistive material. In others, the sensor array may include a substrate adjacent to a combination of the first and second arrays of conductive traces and the piezoresistive material; the force focusing elements being formed on the substrate. The force focusing elements may be convex features on the substrate. The substrate may be part of an environmental protection enclosure for the combination of the first and second arrays of conductive traces and the piezoresistive material.

According to some implementations, the sensor array includes a first substrate adjacent to the combination of the first and second arrays of conductive traces and the piezoresistive material on an opposite side of the combination from a second substrate. One of the first substrate or the second substrate has a plurality of structural elements extending therefrom at least partially through the piezoresistive material in spaces between the conductive traces. In some implementations, the structural elements extend all of the way through the piezoresistive material and contact the other of the first substrate or the second substrate without force exerted on the surface of the sensor array. In others, the structural elements extend only part of the way through the piezoresistive material. The first and second substrates may be part of an environmental protection enclosure for the combination of the first and second arrays of conductive traces and the piezoresistive material.

According to some implementations, the piezoresistive material includes a plurality of apertures each of which is aligned with a space between the conductive traces of the first and second arrays. In some implementations, the sensor array includes a first substrate adjacent to the combination of the first and second arrays of conductive traces and the piezoresistive material on an opposite side of the combination from a second substrate. One of the first substrate or the second substrate has a plurality of structural elements extending therefrom at least partially through the apertures of the piezoresistive substrate. The structural elements may have a form factor substantially conforming to a shape of the apertures.

According to some implementations, the piezoresistive material is a flexible piezoresistive material. In some implementations, the first and second arrays of conductive traces may be formed on the piezoresistive material; either on only one side of the piezoresistive material, or on both sides of the piezoresistive material. In others, one or both of the first and second arrays of conductive traces may be formed on one or more substrates adjacent to the piezoresistive material.

According to another class of implementations, a sensor array includes a first array of conductive traces aligned with a first dimension of the sensor array. The conductive traces of the first array are characterized by a first conductivity. The sensor array includes a second array of conductive traces aligned with a second dimension of the sensor array. The conductive traces of the second array are characterized by a second conductivity higher than the first conductivity. A piezoresistive material provides electrical connectivity between the conductive traces of the first and second arrays. Associated circuitry is configured to apply drive signals to the first array of conductive traces, to receive detection signals from the second array of conductive traces, and to determine one or more locations of one or more corresponding touch events on a surface of the sensor array using the drive and detection signals. The circuitry is further configured to drive one end of a first conductive trace of the first array with a first signal, and to drive an opposing end of the first conductive trace with a second signal. The circuitry receives a mixed signal from a second conductive trace of the second array. The mixed signal includes contributions from the first and second signals via the piezoresistive material. The circuitry is further configured to determine a first location of a first touch event along the first conductive trace with reference to a first value representing the contributions of the first and second signals to the mixed signal.

According to some implementations, the circuitry is further configured to determine one or more additional locations of one or more additional touch events along any of the conductive traces of the first array that are substantially simultaneous with the first touch event with reference to one or more additional values representing one or more additional mixed signals received from one or more of the conductive traces of the second array.

According to some implementations, the circuitry is further configured to determine the first location of the first touch event as being along the first conductive trace and between adjacent conductive traces of the second array. According to some implementations, the circuitry is configured to determine the first location of the first touch event with reference to an additional value representing an additional mixed signal received from an additional conductive trace of the second array.

According to some implementations, the circuitry is further configured to determine a second location of second touch event along the first conductive trace that is substantially simultaneous with the first touch event with reference to the first value and an additional value representing an additional mixed signal received from an additional conductive trace of the second array.

According to some implementations, the circuitry is further configured to drive one end of a third conductive trace of the first array with the first signal, and to drive an opposing end of the third conductive trace with a third signal. The mixed signal also includes additional contributions from the first signal and the third signal corresponding to a second touch event near the third conductive trace that is substantially simultaneous with the first touch event. The circuitry is further configured to generate the first value with reference to the additional contributions from the first and third signals corresponding to the second touch event.

According to some implementations, the circuitry is configured to resolve the first location of the first touch event to one of a plurality of discrete locations associated with the first conductive trace on the surface of the sensor array.

According to some implementations, the conductive traces of the first array are resistive traces, and the circuitry is configured to energize each of the conductive traces of the first array by simultaneously driving opposing ends of the conductive trace with first and second signals, respectively, using a plurality of signal busses. Each signal buss is connected to a plurality of the conductive traces of the first array. The opposing ends of each conductive trace of the first array are connected to a unique pair of the busses. According to some implementations, the conductive traces of the second array are characterized by substantially zero resistance, and at least some of the locations at which the circuitry is configured to determine touch events are along corresponding ones of the conductive traces of the first array and between respective pairs of the conductive traces of the second array.

According to some implementations, the circuitry is configured to resolve detected touch events to a plurality of discrete locations on the surface of the sensor array. The plurality of discrete locations form an array of Y discrete locations along the first dimension by X discrete locations along the second dimension. The first array of conductive traces includes X conductive traces, and the second array of conductive traces includes fewer than Y conductive traces. X and Y are integers greater than zero.

According to some implementations, is configured to resolve detected touch events to a plurality of discrete locations on the surface of the sensor array. The plurality of discrete locations forms an array of Y discrete locations along the first dimension by X discrete locations along the second dimension. The first array of conductive traces includes X conductive traces. X and Y are integers greater than zero. The sensor array further includes a plurality of busses by which the circuitry applies the drive signals to the first array of conductive traces. The plurality of busses includes fewer than X busses.

According to some implementations, the piezoresistive material is a flexible piezoresistive substrate. According to some implementations, the first and second arrays of conductive traces are formed on the flexible piezoresistive substrate. According to some implementations, the first and second arrays of conductive traces are formed on only one side of the flexible piezoresistive substrate. According to others, the first and second arrays of conductive traces are formed on both sides of the flexible piezoresistive substrate. According to some implementations, one or both of the first and second arrays of conductive traces are formed on one or more additional substrates adjacent to the flexible piezoresistive substrate.

As will be appreciated by those of skill in the art, various combinations of the foregoing features and functionalities are within the scope of this disclosure. A further understanding of the nature and advantages of various implementations may be realized by reference to the remaining portions of the specification and the drawings.

DETAILED DESCRIPTION

Two-dimensional sensor arrays incorporating piezoresistive materials are described in this disclosure. Specific implementations are described below including the best modes contemplated. Examples of these implementations are illustrated in the accompanying drawings. However, the scope of this disclosure is not limited to the described implementations. Rather, this disclosure is intended to cover alternatives, modifications, and equivalents of these implementations. In the following description, specific details are set forth in order to provide a thorough understanding of the described implementations. Some implementations may be practiced without some or all of these specific details. In addition, well known features may not have been described in detail to promote clarity.

Piezoresistive materials include any of a class of materials that exhibits a change in electrical resistance in response to mechanical force or pressure applied to the material. A signal representative of the magnitude of the applied force is generated based on the change in resistance. This signal is captured via conductive traces (e.g., as a voltage or a current with the piezoresistive material as part of a divider circuit), digitized (e.g., via an analog-to-digital converter), processed (e.g., by an associated processor or controller or suitable control circuitry), and mapped (e.g., by the associated processor, controller, control circuitry, or a connected computing system) to a control function that may be used in conjunction with virtually any type of process, device, or system.

Figure 1A:
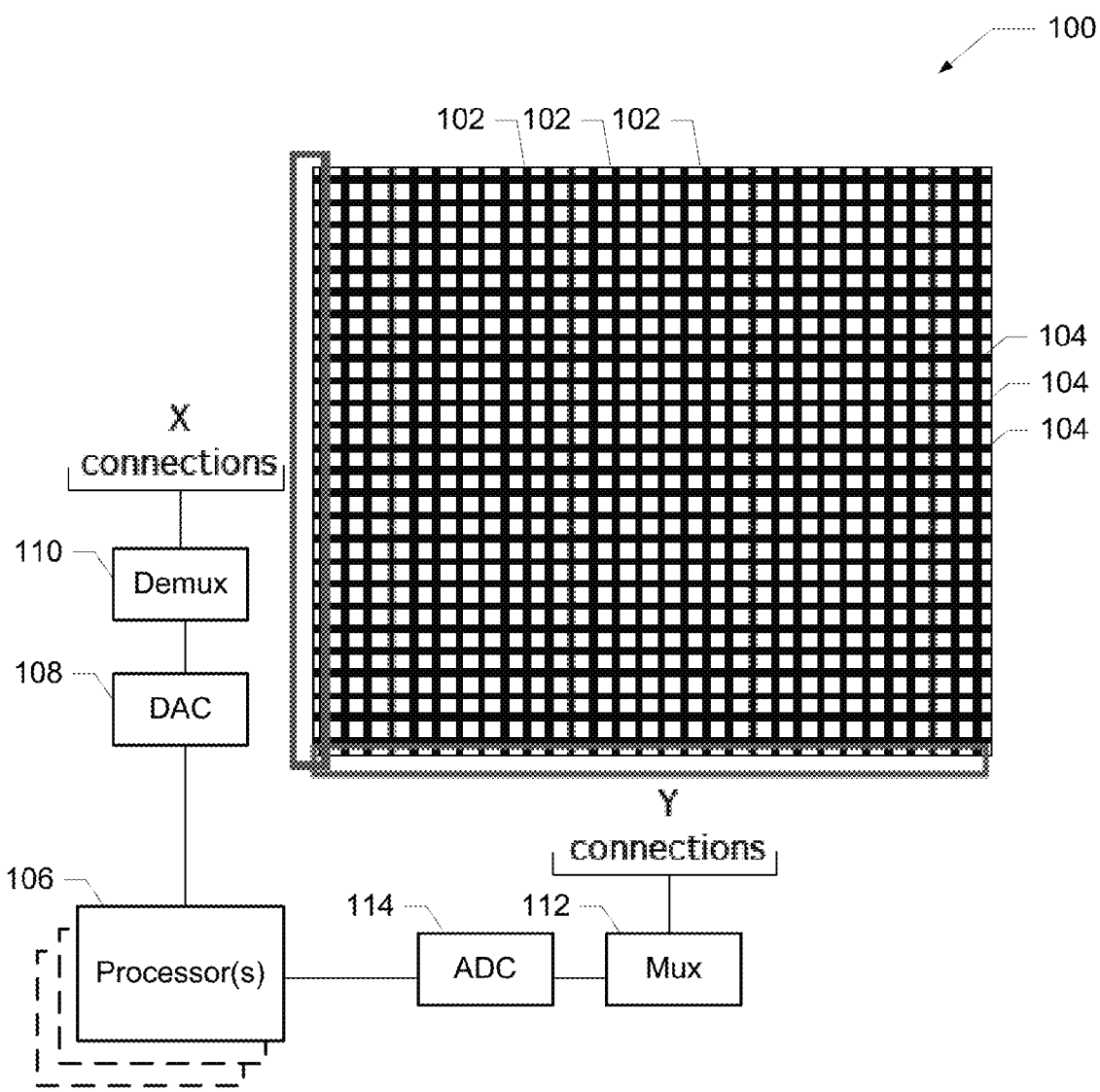
FIGS. 1A and 1B are simplified representations of two-dimensional sensor arrays.

FIG. 1A shows an example of a two-dimensional sensor array 100 that includes a set of substantially parallel conductive traces 102 oriented in one direction, and another set of substantially parallel conductive traces 104 oriented at about 90 degrees to the first set of traces. Traces 102 and traces 104 are electrically connected via a piezoresistive material (not shown for clarity). The traces and the piezoresistive material may be positioned relative to each other in a number of ways. For example, the piezoresistive material may be a fabric or other flexible substrate and the traces may be formed on the piezoresistive material on opposite sides of the material. In another example, the piezoresistive material might be sandwiched between two substrates on which the traces are formed or of which they are a part. In yet another example, both arrays of traces may be on the same side of a piezoresistive substrate (formed either on the piezoresistive material or separately from the piezoresistive material on or as part of an adjacent substrate) with insulation between the traces where they intersect or coincide. Additional substrates that are adjacent the piezoresistive material may also be fabric or other flexible materials. In implementations in which traces are formed on or part of one or more such substrates, the piezoresistive material may be coupled (e.g., laminated) to the additional substrate(s) to form a multilayer structure. Other suitable variations are within the scope of this disclosure.

By sequentially driving the traces of one set (e.g., using processor(s) 106, digital-to-analog converter 108, and demultiplexer 110), and sequentially scanning the traces of the other (e.g., using multiplexer 112, analog-to-digital converter 114, and processor(s) 106), both the position and force of a touch event on the array can be detected. And because of the sequential selection and activation of the traces, such a configuration is capable of detecting multiple touch events substantially simultaneously. As will be understood, the applications for such sensor arrays are virtually limitless.

Figure 1B:
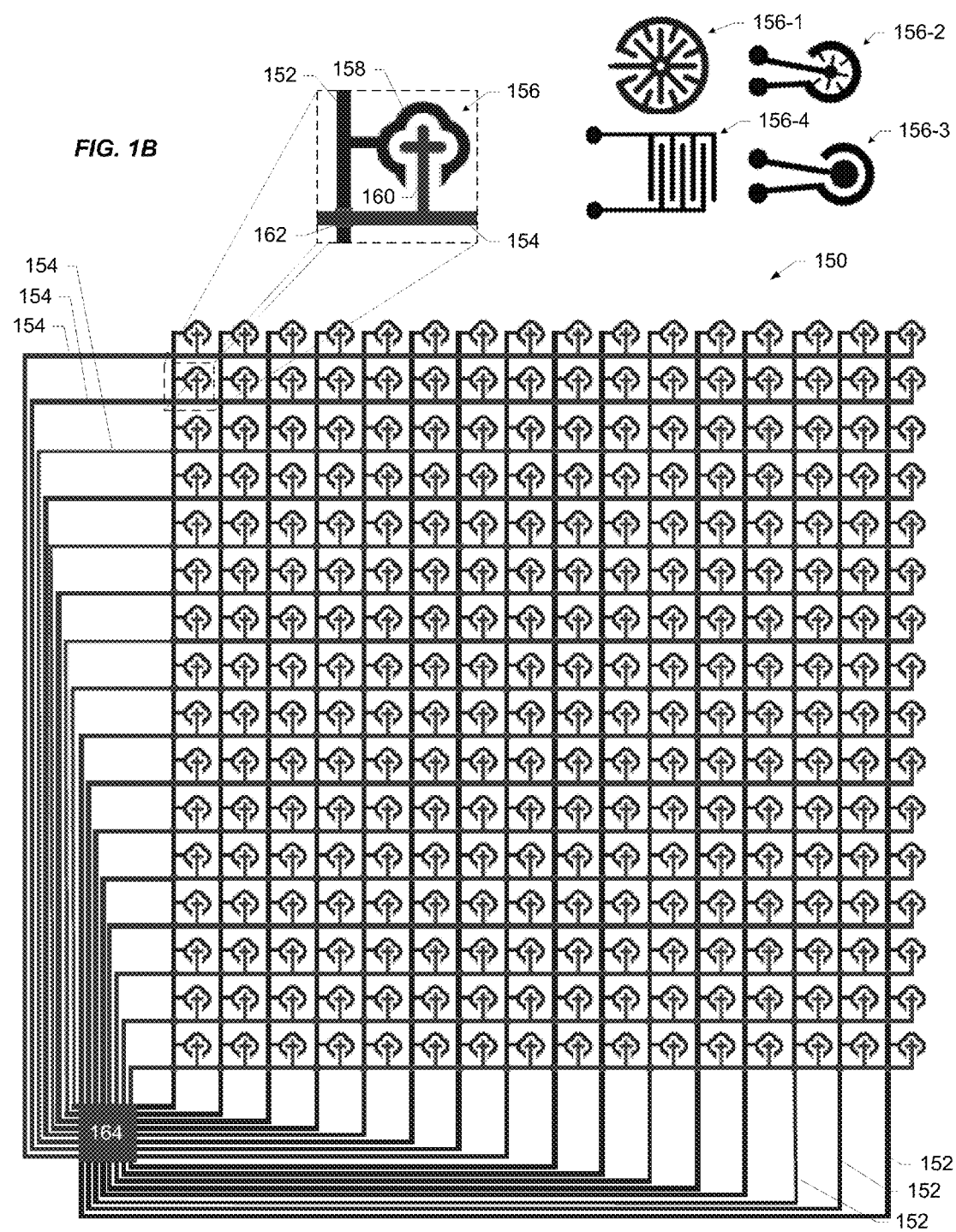

FIG. 1B shows another example of a two-dimensional sensor array 150 that includes a set of substantially parallel conductive traces 152 oriented in one direction, and another set of substantially parallel conductive traces 154 oriented at about 90 degrees to the first set of traces. Sensor trace patterns 156 are provided near the intersections of the horizontal and vertical traces; each pattern including a trace 158 connected to one of the vertical traces 152, and a trace 160 connected to one of the horizontal traces 154. The depicted example employs a cruciform shape for trace 160 and a clover shape for trace 158 that provides a significant area in which the two conductive traces of the pattern are in close proximity to each other. As will be appreciated, the shapes of traces 158 and 160 and the distance(s) between them may be controlled to achieve a desired sensitivity (dynamic range) for a given application. Examples of other traces patterns that may be suitable for particular applications (e.g., 156-1 through 156-4) are shown. A variety of other configurations are within the scope of this disclosure.

Traces 152 and 158 are electrically connected with traces 154 and 160 via a piezoresistive material (not shown for clarity). According to some implementations of sensor array 150, the arrays of parallel traces and the trace patterns are formed on one side of the piezoresistive material (either on the piezoresistive material or on a substrate that is adjacent the piezoresistive material). In such implementations insulating material 162 is provided at the intersections of the parallel traces 152 and 154 to insulate these traces from each other. However, it should be understood that, as with sensor array 100, implementations are contemplated in which the traces of the respective arrays are disposed on opposite sides of intervening piezoresistive material (e.g., traces 152 and 158 on one side of the material and traces 154 and 160 on the other).

Sensor array 150 has associated circuitry 164 (which may be similar to the circuitry shown in FIG. 1A) configured to apply drive signals to one set of conductive traces and to receive detection signals from the other. As discussed above with reference to sensor array 100, sequential selection and activation of the traces by circuitry 164 enables detection of the position and force of a touch event on the array, as well as the detection of multiple simultaneous touch events.

According to some implementations, the signal quality for touch events on two-dimensional arrays such as arrays 100 and 150 may be improved by connecting other traces in the array to a known potential (e.g., ground) when a signal from a particular trace is being read (rather than leaving them floating). This may reduce contributions from touch events associated with the other vertical traces.

According to a particular class of implementations, conductive traces are printed, screened, deposited, or otherwise formed onto flexible piezoresistive material. As will be appreciated, this allows for the creation of a sensor array that fits any arbitrary shape or volume. The piezoresistive material may be any of a variety of woven and non-woven fabrics having piezoresistive properties. Implementations are also contemplated in which the piezoresistive material may be any of a variety of flexible materials (e.g., rubber, or a stretchable fabric such as spandex) having piezoresistive properties. The conductive traces may be arranged in a variety of ways depending on the shape or volume to which the array is designed to conform. For example, the rectilinear configurations shown in FIGS. 1A and 1B may be suitable for substantially flat implementations, while varying degrees of curvature of the traces and/or shaping of the overall shape of the array may be desired for arrays conforming to other types of surfaces or shapes. According to some implementations, only portions of an array might be used to enable the folding or rolling up of the array into a desired form factor, e.g., if the upper right hand corner of array 150 is removed, the remainder of the array could be rolled into a conical shape. Other such Euclidean transformations to achieve different shapes and form factors are within the scope of this disclosure.

The traces may be formed using any of a variety of conductive inks or paints. Implementations are also contemplated in which the conductive traces are formed using any flexible conductive material that may be formed on the flexible piezoresistive material. It should therefore be understood that, while specific implementations are described with reference to specific materials and techniques, the scope of this disclosure is not so limited.

Both one-sided and two-side implementations are contemplated, e.g., conductive traces can be printed on one or both sides of the piezoresistive fabric. As will be understood, two-sided implementations may require some mechanism for connecting conductive traces on one side of the fabric to those on the other side. Some implementations may use vias in which conductive ink or paint is flowed through the via to establish the connection. Alternatively, metal vias or rivets may make connections through the fabric.

Both single and double-sided implementations may use insulating materials formed over conductive traces. This allows for the stacking or layering of conductive traces and signal lines, e.g., to allow the routing of signal line to isolated structures in a manner analogous to the different layers of a PCB.

Routing of signals on and off the piezoresistive fabric may be achieved in a variety of ways. A particular class of implementations uses elastomeric connectors (e.g., ZEBRA® connectors) which alternate conductive and nonconductive rubber at a density typically an order of magnitude greater than the width of the conductive traces to which they connect (e.g., at the edge of the fabric). Alternatively, a circuit board made of a flexible material (e.g., Kapton), or a bundle of conductors may be riveted to the fabric. The use of rivets may also provide mechanical reinforcement to the connection.

Matching conductive traces or pads on both the piezoresistive material and the flexible circuit board can be made to face each. A layer of conductive adhesive (e.g., a conductive epoxy such as Masterbond EP79 from Masterbond, Inc. of Hackensack, N.J.) can be applied to one of the surfaces and then mated to the other surface. The conductive traces or pads can also be held together with additional mechanical elements such as a plastic sonic weld or rivets. If conductive rivets are used to make the electrical connections to the conductive traces of the piezoresistive fabric, the conductive adhesive may not be required. Conductive threads may also be used to connect the conductive traces of the fabric to an external assembly.

According to a some implementations, the piezoresistive material is a pressure sensitive fabric manufactured by Eeonyx, Inc., of Pinole, Calif. The fabric includes conductive particles that are polymerized to keep them suspended in the fabric. The base material is a polyester felt selected for uniformity in density and thickness as this promotes greater uniformity in conductivity of the finished piezoresistive fabric. That is, the mechanical uniformity of the base material results in a more even distribution of conductive particles when a slurry containing the conductive particles is introduced. Calendared material presents a smoother outer surface which promotes more accurate screening of conductive inks than a non-calendared material. The fabric may be woven. Alternatively, the fabric may be non-woven such as, for example, a calendared fabric e.g., fibers, bonded together by chemical, mechanical, heat or solvent treatment.

The conductive particles in the fabric may be any of a wide variety of materials including, for example, silver, copper, gold, aluminum, carbon, etc. Some implementations may employ carbon graphenes that are formed to grip the fabric. Such materials may be fabricated using techniques described in U.S. Pat. No. 7,468,332 for Electroconductive Woven and Non-Woven Fabric issued on Dec. 23, 2008, the entire disclosure of which is incorporated herein by reference for all purposes. However, it should again be noted that any flexible material that exhibits a change in resistance or conductivity when pressure is applied to the material and on which conductive traces may be printed, screened, deposited, or otherwise formed will be suitable for implementation of sensor arrays as described herein.

According to a particular class of implementations, conductive traces having varying levels of conductivity are formed on the piezoresistive material using conductive silicone-based inks manufactured by, for example, E.I. du Pont de Nemours and Company (DuPont) of Wilmington, Del., and/or Creative Materials of Ayer, Mass. An example of a conductive ink suitable for implementing highly conductive traces for use with various implementations is product number 125-19 from Creative Materials, a flexible, high temperature, electrically conductive ink. Examples of conductive inks for implementing lower conductivity traces for use with various implementations are product numbers 7102 and 7105 from DuPont, both carbon conductive compositions. Examples of dielectric materials suitable for implementing insulators for use with various implementations are product numbers 5018 and 5036 from DuPont, a UV curable dielectric and an encapsulant, respectively. These inks are flexible and durable and can handle creasing, washing, etc. The degree of conductivity for different traces and applications is controlled by the amount or concentration of conductive particles (e.g., silver, copper, aluminum, carbon, etc.) suspended in the silicone. These inks can be screen printed or printed from an inkjet printer. Another class of implementations uses conductive paints (e.g., carbon particles mixed with paint) such as those that are commonly used for EMI shielding and ESD protection.

The dynamic range of a two-dimensional sensor array implemented as described herein may be manipulated through the use of a variety of mechanical structures that may be included in or on any of the layers, substrates, or components of the array. Such structures may be flexible (e.g., silicone) components or features, the characteristics of which (e.g., shape, size, height, flexibility, number, placement, etc.) may be manipulated to provide resistance to applied physical forces such that a desired dynamic range of the sensors is achieved. Some examples of such structures are described below with reference to FIG. 4. A wide variety of other structures and components suitable for achieving a desired sensitivity or dynamic range are within the scope of the disclosure.

As will be understood by those of skill in the art, a variety of techniques may be employed to acquire data from sensors constructed as described herein. Some of these techniques may involve a simple measurement of a change in resistance (as determined from a voltage or current measurement) between two coinciding conductive traces having the same or similar conductivity. However, for sensors having arrays that include many conductive traces, this may require an unacceptable number of signal lines to route signals both to and from the sensor array. For example, for the implementation of FIG. 1A having X traces 104 and Y traces 102, the number of signal lines to the associated circuitry would be X+Y. As will be understood, for very large arrays this may become difficult to implement. Therefore, according to a particular class of implementations, conductive traces formed on piezoresistive material and having different levels of conductivity are driven and interrogated with signal patterns that reduce the number of signal lines required to achieve sensor configurations that are sensitive to location, pressure, direction, and velocity of applied force.

Figure 2:
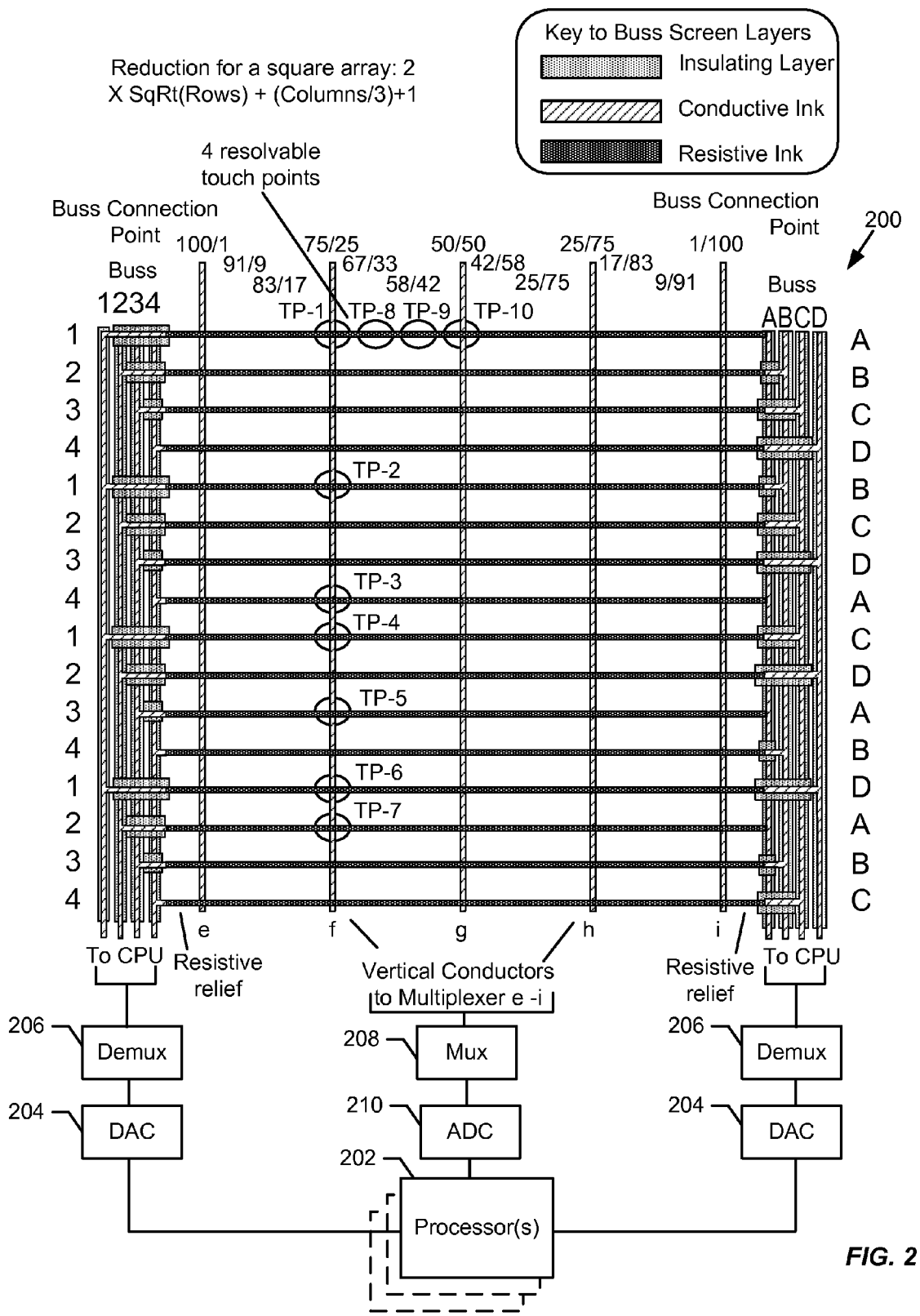
FIG. 2 is another simplified representation of a two-dimensional sensor array.

FIG. 2 illustrates a particular implementation of a two-dimensional sensor array 200 that includes an array of parallel traces that are highly conductive (e.g., near zero resistance) oriented in a first direction (vertically in the figure), and an array of parallel traces that are less conductive (e.g., about 500 to 1000 ohms each from end to end) oriented in a second direction (horizontally in the figure). Electrical connections between the traces are made via a piezoresistive material (not shown for clarity). As with the implementation described above with reference to FIGS. 1A and 1B, the traces and the piezoresistive material may be positioned relative to each other in a variety of ways. Further, the conductive traces may be configured to conform to a particular surface or volume. So, although the implementation of FIG. 2 illustrates a rectilinear array of traces that are formed on opposite sides of a piezoresistive substrate, the scope of this disclosure is not so limited.

Drive signals generated by processor(s) 202 are transmitted to the horizontal traces via digital-to-analog converter 204, de-multiplexer 206, and busses 1-4 and A-D. Each horizontal trace is designated by the pair of busses to which it is connected, i.e., the top horizontal trace in FIG. 2 is trace 1A, the next trace down is trace 2B, and so on. No two horizontal traces are connected to the same pair of busses. Signals are received by processor(s) 202 from vertical traces e-i via multiplexer 208, and analog-to-digital converter 210. The resolution of the array along the vertical axis is determined by the number and spacing of the horizontal traces. That is, the location of a touch event along this axis is determined by the location of the horizontal trace for which it detected. However, as will be discussed, the resolution along the horizontal axis is greater than what is possible with the depicted number and spacing of the vertical traces using conventional techniques.

In addition, as will be appreciated from the figure, the number of signal lines that must be routed to and from array 200 is many fewer than what is required for conventional arrays of comparable resolution. That is, a two-dimensional array typically has one signal line for each horizontal and each vertical channel, e.g., requiring X+Y signal lines to be routed off the array. By contrast, in the example illustrated in FIG. 2, array 200 requires only 8 signal lines for 16 horizontal traces, and only 5 signal lines for vertical traces that provide a resolution along the horizontal axis that would require many more vertical traces in a conventional array. This may be achieved as follows.

Figure 3:
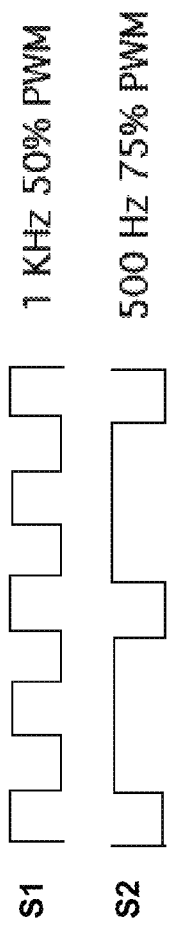
FIG. 3 illustrates examples of drive signals for use with the two-dimensional sensor array of FIG. 2.
Figure 3:
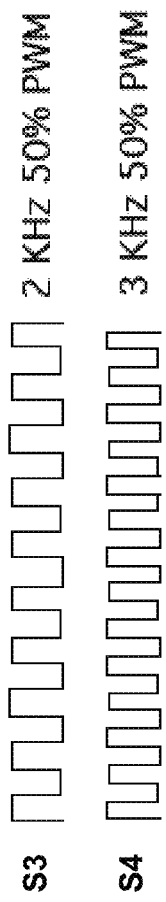

In operation, each horizontal trace is energized in succession by simultaneously driving the opposing ends of the trace with primary detection signals S1 and S2 (shown in FIG. 3). While each horizontal trace is energized, signals are read from the vertical traces in succession. The force of a touch event on the piezoresistive material reduces the resistance between intersecting traces near the touch point which, depending on its location along the horizontal trace, results in different contributions from signals S1 and S2 measured in a mixed signal on the highly conductive vertical trace. The overall amplitude of the mixed signal represents the magnitude of the force. By determining the relative contributions of S1 and S2 to the mixed signal a horizontal location for the touch point may be determined.

According to a particular implementation and as illustrated in FIG. 3, primary detection signals S1 and S2 are different pulse trains of the same amplitude but with different duty cycles (e.g., S1 at 1 kHz with a 50% duty cycle, and S2 at 500 Hz with a 75% duty cycle), with the phases of the two pulse trains synchronized as shown. Location information may be derived from the mixed signal measured on the vertical conductive trace as follows. The signal on the vertical trace is sampled by A/D converter 210 (e.g., oversampled by a factor of two or more relative to the frequency of the inputs). For processor(s) 202, an inexpensive, general-purpose processor may be employed that can read up to 40 signals with up to 10-bits of resolution, and take 500K samples per second. The same general processor may drive the conductive traces. As will be appreciated, having the same processor generate the signals and perform the A/D conversion simplifies timing of samples to coincide with changes of the drive states. It also reduces the overall space or volume taken up by these components and keeps costs down. Thus, large arrays may be constructed relatively inexpensively. However, it should also be understood that implementations are contemplated in which different processors may perform these functions. More generally and as will be understood by those of skill in the art, a wide variety of suitable processors, controllers, computing devices, logic devices and other suitable circuitry may be adapted to control the sensors and sensor arrays described herein. Therefore, reference to specific circuitry or devices should not be used to limit the scope of this disclosure.

Figure 4:
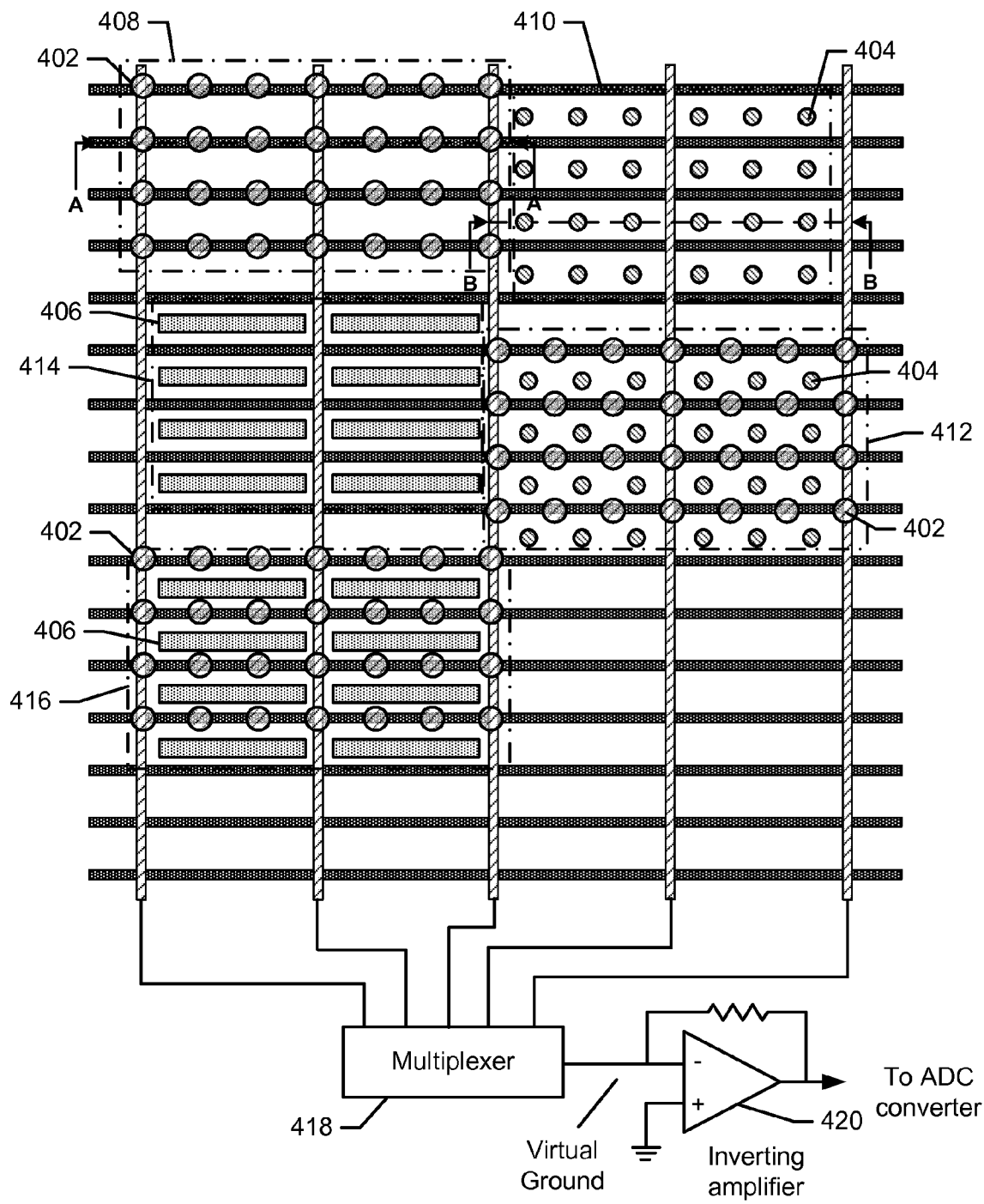
FIG. 4 illustrates examples of a variety of mechanical features for use with two-dimensional sensor array.

According to some implementations and as shown in FIG. 4, the vertical traces go through a multiplexer 418 and into an inverting operational amplifier 420 that represents a virtual ground reference. As a result, the signal (e.g., a current) measured on any one of the vertical traces will experience the lowest impedance to a ground reference and be accurately representative of any nearby touch events in that contributions from more remote touch events on the array have a much higher resistive path and are dominated by the contributions from local events.

The processor evaluates specific amplitudes at specific times that are correlated with the values of signals S1 and S2 at those times. The relative contribution from each signal is determined by selecting closely-spaced samples of the mixed signal at times when the respective signals are each known to have a particular value or characteristic, e.g., full amplitude. The ratio of those two measurements represents the relative contributions of each signal to the mixed signal that, in turn, can be mapped to a location between the end points of the trace. Examples of ratios of the contributions of signals S1 and S2 representing different touch points along the horizontal axis are shown in FIG. 2, e.g., 75/25 corresponding to touch point TP-1, 67/33 corresponding to touch point TP-8, and so on. The pressure or force of the touch event can be determined by measuring peak values of the sampled mixed signal. Thus, both the locations and forces of touch events along the horizontal traces may be determined at touch points (TPs) that are between the vertical traces.

The resolution along the horizontal axis with which touch points may be detected may vary for different implementations. According to some implementations, the resolution may be very high with very precise locations determined. Alternatively and according to a particular class of implementations, the resolution may be designed to be appropriate for particular applications by quantizing the touch point locations. In such implementations, each horizontal trace may be thought of as a series of segments that each resolve to a particular touch point location along that trace. Quantization simplifies the detection of touch events by reducing the number of allowable locations to which the measured ratios map. For example, according to a particular implementation, there are only three allowable locations for each vertical trace along a particular horizontal trace; i.e., at the vertical trace itself and at locations immediately to its left and right. This may be understood with reference to FIG. 2.

In the depicted example, touch points TP-1, TP-8, TP-9 and TP-10 represent resolvable touch points along horizontal trace 1A. That is, any touch events falling along the segment of trace 1A within a particular one of the touch point ovals is resolved to the center of that segment. Put another way, the determined ratio of the relative contributions to the measured signal from primary detection signals S1 and S2 corresponds to a particular touch point if that ratio falls within a range of values associated with that touch point, e.g., TP-8 might correspond to values between 71/29 and 63/37. In this example then, each vertical trace may be used to detect 3 touch points along each horizontal trace, i.e., one at the trace and one on other side.

As will be appreciated, there may be situations in which the value derived from the signal on any one vertical trace may be ambiguous. For example, a single touch point at TP-8 might be indistinguishable from two simultaneous touch points at TP-1 and TP-9 if only the signal on vertical trace f is considered. Therefore, according to some implementations, the processor can distinguish between these two cases with reference to the values derived from signals on other vertical traces that are close in time. In this example, the signal on vertical trace g would be different for the single touch point case than it is for the two touch points due to the proximity of touch point TP-9.

Thus, the processor can use multiple values derived from adjacent vertical traces to disambiguate among various scenarios. More generally, implementations are contemplated in which the processor is configured to take into account multiple data points (separated in space and/or time) in order to accurately and reliably discriminate between scenarios that might otherwise be ambiguous. Another example of a technique that may be employed to disambiguate touch event scenarios involves connecting other vertical traces to a known potential (e.g., ground) when a particular vertical trace is being read (rather than leaving them floating). As discussed above with reference to the implementations of FIGS. 1A and 1B, this may reduce contributions from touch events associated with the other vertical traces. And as discussed in greater detail below, mechanical elements can be introduced that promote the quantization of touch point locations and may serve to further promote disambiguation.

According to some implementations, ambiguity may also be dealt with by generating multiple values for each vertical trace signal while a particular horizontal trace is energized. For example, horizontal trace 1A may be energized with signal S1 applied via buss 1 and signal S2 applied via buss A. Values are then successively generated by the processor for the signals received on vertical traces e-i. Horizontal trace 1A may then be energized by reversing the two primary detection signals (signal S1 on buss A and signal S2 on buss 1) and generating another set of values for the signals on traces e-i. This second set of values may be generated immediately following generation of the first set of values, or on a successive loop through all of the horizontal traces. As will be appreciated, this additional information may be used by the processor for discriminating between potentially ambiguous scenarios. For example, for a touch event at a particular touch point the same ratio of signal contribution should be determined regardless of the trace ends to which signals S1 and S2 are applied. The duplicative data may therefore be used to verify or validate the first data. Alternatively, the duplicate data values for a particular combination of horizontal and vertical trace could be averaged.

It should also be noted that the number and the size of touch points that can be resolved by a single vertical trace may vary. For example, the size of the touch points may correspond to the size of the average human fingertip. Alternatively, the size of the touch points may correspond to smaller instruments such as the tips of styluses or pointers. In addition, more than three touch points (e.g., 5 or 7) may be resolved by each vertical trace. It should also be noted that the number of touch points that may be resolved may also be constrained by the uniformity and consistency of the resistance of both the piezoresistive material and the horizontal traces, i.e., the greater the uniformity and/or consistency of these components, the greater the resolution that may be supported. On the other hand, because the values being generated are ratios (at least for touch event locations), as long as the resistance of a horizontal trace is relatively consistent along its length, there need not be a high level of consistency from one horizontal trace to the next.

As will be appreciated with reference to the foregoing, the techniques described herein may result in a significant reduction in signal lines required to bring signals to and from the array relative to conventional arrays of comparable resolution. However, as will also be appreciated, there may be scenarios in which multiple touch events occurring along the same vertical trace result in potentially ambiguous data. For example, touch events might occur simultaneously at touch points TP-1 and TP-2 in FIG. 2. When horizontal trace 1A is energized and the signal on vertical trace f is captured, there will be contributions to the captured signal from both touch events. That is, the touch event at touch point TP-1 will result in contributions from primary detection signals S1 and S2 in the mixed signal on trace f as described above. In addition, because buss 1 is also driven by signal S1, there will be a contribution to the signal on trace f from the touch event at TP-2 along horizontal trace 1B. Similarly, when trace 1B is selected for energizing, there will be contributions from both touch events in that data as well.

Therefore, according to some implementations, "ghost" detection signals are introduced in the array simultaneous with the primary detection signals. These signals allow the processor to account for any unwanted contributions from simultaneous events along the same vertical trace so that it can generate an accurate representation of any touch events along the primary horizontal trace being energized. The way in which this may be achieved may be understood with reference to FIGS. 2 and 3.

In this example, the primary horizontal trace being energized with primary detection signals S1 and S2 is trace 1A (i.e., the topmost trace in the figure), and the vertical trace for which a signal is being captured is trace f. Because buss 1 must be active for trace 1A to be energized, it is possible for unwanted contributions to the signal on trace f from signal S1 to come from touch events at TP-2, TP-4 and TP-6. Similarly, because buss A must also be active, unwanted contributions from signal S2 may result from touch events at TP-3, TP-5 and TP-7.

To account for the unwanted contribution from any touch event at TP-2, ghost detection signal S3 is introduced on buss B while trace 1A is energized. As discussed above, a touch event at touch point TP-2 may be represented by a ratio that represents the relative contributions of signals S1 and S3 at vertical trace f. Because this relationship is known, i.e., 75/25, and because the magnitude of the contribution from signal S3 is also known (because it is measured in isolation), the magnitude of the contribution from signal S1 due to a touch event at TP-2 may be determined and accounted for when calculating the values for a touch event at or near TP-1. Similarly, to account for the unwanted contribution from any touch event at TP-7, ghost detection signal S4 is introduced on buss 2 (not simultaneous with signal S3 on buss B because that would energize trace 2B).

In the depicted example, signal S3 is a 2 kHz signal with a 50% duty cycle, and signal S4 is a 3 kHz signal also with a 50% duty cycle. It will be understood that these are merely representative examples and that a wide range of alternatives may be employed for different applications; as long as the timing and amplitudes of the signals are such that the relative contributions of the various signals to a particular mixed signal can be determined as described.

To account for unwanted contributions for all possible touch events along vertical trace f while horizontal trace 1A is energized, ghost detection signals S3 and S4 are successively introduced for each touch point along vertical trace f for which such a contribution might occur. Thus, signal S3 is introduced successively to busses B, C and D to account for touch points TP-2, TP-4 and TP-6, respectively; and signal S4 is introduced successively to busses 4, 3 and 2 to account for touch points TP-3, TP-5 and TP-7, respectively. Ghost detection signals are introduced in a similar manner for each signal capture on vertical traces e-i. And this is done for each horizontal trace. Those of skill in the art will understand how to extrapolate from the foregoing discussion to account for all possible combinations of multiple touch events along any of the vertical traces.

As an alternative, instead of using two different ghost detection signals that are successively introduced, implementations are contemplated in which a sufficient number of unique ghost detection signals are simultaneously introduced. As another alternative, a single ghost detection signal can be introduced sequentially to all of the relevant busses (assuming the far side of the buss is grounded). In such implementations, the magnitude of the detected ghost signal would be stored while the ground and ghost detection signal are exchanged so that the ratio can then be computed.

Returning to the example in which horizontal trace 1A is energized, once all contributions to the signal on vertical trace f from other possible touch points along the vertical trace are identified, the unwanted contributions may be removed (e.g., subtracted) from the value being determined so that the horizontal position of any touch event along trace 1A (if any) may be determined from the resulting ratio as described above.

As each successive horizontal trace is energized, a pair of values is generated for each combination of an energized trace with each of the vertical traces. One value in the pair represents the relative contributions of the primary detection signals to the signal received on the vertical trace (e.g., expressed as a ratio), and the other the amplitude or magnitude of that signal (e.g., expressed as a value that is proportional to the force of the touch event; at least within the dynamic range of the piezoresistive material). In the example of array 200 of FIG. 2, a single pass through the array would result in a data set having 80 pairs of such values, i.e., 5 pairs of values for each of 16 horizontal traces. Each of these pairs of values may or may not represent a touch event. The ways in which the data may be processed to determine whether or not a pair of values represents a meaningful event, i.e., a touch event, may vary considerably.

For example, in some implementations, a pair of values may be considered a touch event if the amplitude or magnitude value for the pair (e.g., a peak measurement of the received signal) exceeds a threshold. The threshold may be fixed or dynamic. For example, the threshold might be determined using an average of the amplitude measurements made across the array over a given time period (e.g., corresponding to a single pass through the array). If the amplitude value for a given pair of values exceeds the threshold, the pair of values is considered to represent a touch event, and the location of the touch event is determined with reference to the ratio value of the pair (e.g., mapped to a quantized touch point as discussed above).

Figure 6:
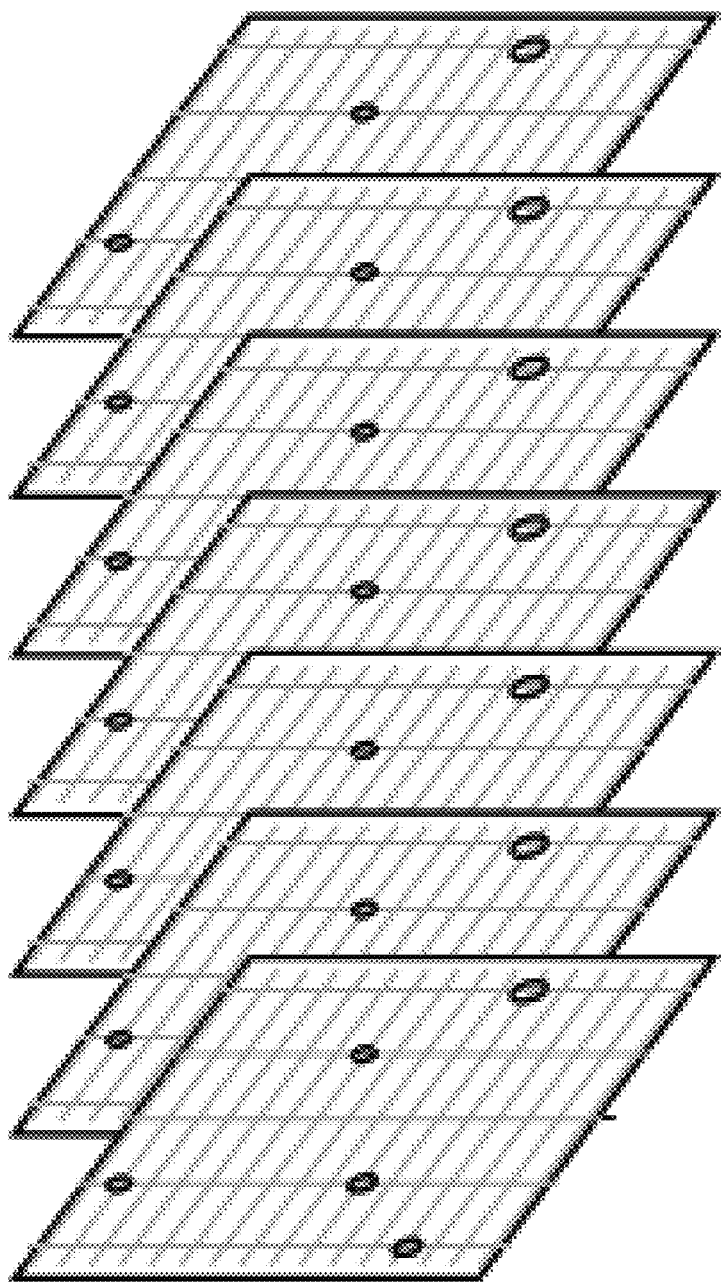
FIG. 6 provides a representation of data sets for a two-dimensional sensor array generated over time.

According to some implementations, the reliability with which touch events are detected may be enhanced by comparing the data sets generated by successive passes or "scans" through the array over time. A scan corresponds to energizing each of the horizontal traces once and reading signals from each of the vertical traces once for each horizontal trace. For a particular implementation of the example of FIG. 2, 5 signal reads (corresponding to vertical traces e-i) may occur for each of the 16 horizontal traces each scan. As discussed above, this results in 10 values for each horizontal trace; 5 ratios representing the relative contributions of signals S1 and S2 and 5 amplitudes representing the force of any touch events. Each set of 160 values may be thought of as a "frame" of data that may be compared to one or more previous and/or subsequent frames for the purpose of more accurately and reliably detecting touch events. This is illustrated in FIG. 6 in which 7 successive frames of data are represented.

According to some implementations, techniques developed for the processing of frames of video may be adapted to make detection of touch events more robust and reliable. For example, the primary and ghost detection signals described above with reference to FIG. 2 may be thought of like the RGB color components of a video frame with the strengths of the respective signals being analogous to the strengths of the RGB contributions. A frame could be saved each time the two primary detection signals are changed to a new resistive trace or reversed and for each iteration of the ghost detection signal states.

With such data methods of processing image data (e.g., for machine vision) would be applicable. Such methods often use versions of wavelet analysis to decompose a video frame. Because of the known constraints of our data (array size, time series) simplified forms of wavelet analysis may be suitable, making it possible to go readily from our input values to a simplified post analysis result.

According to some implementations, machine learning techniques may be employed that use of Markov chains or similar mechanisms to track changes over time. Markov modeling is regularly used to compare present states to previous states, providing specific classifications of the chain. Some implementations may use edge detection along with statistical approaches such as Bayesian methods to analyze data. Because of the highly constrained data sets that may be produced with some implementations, tools from the realm of video analysis lend themselves to robust solutions.

For additional information about signal processing techniques that may be adapted for use with implementations described herein please refer to (1) *Machine Learning for Multimodal Interaction: First International Workshop*; MLMI 2004, Martigny, Switzerland, Jun. 21-23, 2004, Revised Selected Papers (Google eBook); (2) *Automatic Video Object Segmentation Using Wavelet Transform and Moving Edge Detection*; Xiao-Yan Zhang and Rong-Chun Zhao; 2006 International Conference on Machine Learning and Cybernetics, 13-16 (August 2006); (3) *Human detection based on discrete Wavelet transform*; M. M. Deshpande, J. G. Rana, and M. M. Pawar; IET Chennai 3rd International on Sustainable Energy and Intelligent Systems (SEISCON 2012) (27-29 Dec. 2012); (4) *Wavelet-based Image Compression Using Support Vector Machine Learning and Encoding Techniques*; Rakib Ahmed; Proceedings of the 8th IASTED International Conference on Computer Graphics and Imaging (2005); (5) *Video Forensics in Temporal Domain using Machine Learning Techniques*; Sunil Jaiswal and Sunita Dhavale; I. J. Computer Network and Information Security (July 2013); (6) *Content Based Image Classification with Wavelet Relevance Vector Machines*; Arvind Tolambiya, S. Venkataraman, Prem K. Kalra; Soft Computing—A Fusion of Foundations, Methodologies and Applications—Special Issue on Pattern Recognition and Information Processing Using Neural Networks; Volume 14 Issue 2, (September 2009); and (7) *What to believe: Bayesian methods for data analysis*; John K. Kruschke; Trends in cognitive sciences, Volume 14, Issue 7 (July 2007). The entire disclosure of each of the foregoing is incorporated herein by reference for all purposes.

Depending on the application, and in particular for implementations in which traces are formed on a flexible piezoresistive substrate, some form of mechanical and/or environmental protection may be desirable. For example, thin silicone sheets could be laminated over one or both sides of the array.

According to various implementations, the quantization of touch points may be promoted by introducing mechanical structures in and around the array that effectively focus forces on the array toward the desired discrete locations. And as will be discussed, some of these structures may also be useful for optimizing an array for different ranges of applied force, providing mechanical support, promoting alignment of system components, and/or providing environmental protection. Examples of such structures will be discussed with reference to FIGS. 4 and 5.

FIG. 4 shows a section of a two-dimensional sensor array 400 in which various mechanical features are shown in different regions of the array for the purpose of illustration. The depicted features include force focusing elements (e.g., bumps 402), structural elements (e.g., posts 404) and apertures (e.g., cutouts 406). Bumps 402 are illustrated by themselves in region 408. Posts 404 are illustrated by themselves in region 410. Bumps 402 and posts 404 are shown used together in region 412. Cutouts 406 are shown alone in region 414 and in combination with bumps 402 in region 416. As will be appreciated, these regions are merely for illustration and that implementations are contemplated in which some or all of the features are used in various combinations.

Figure 5:
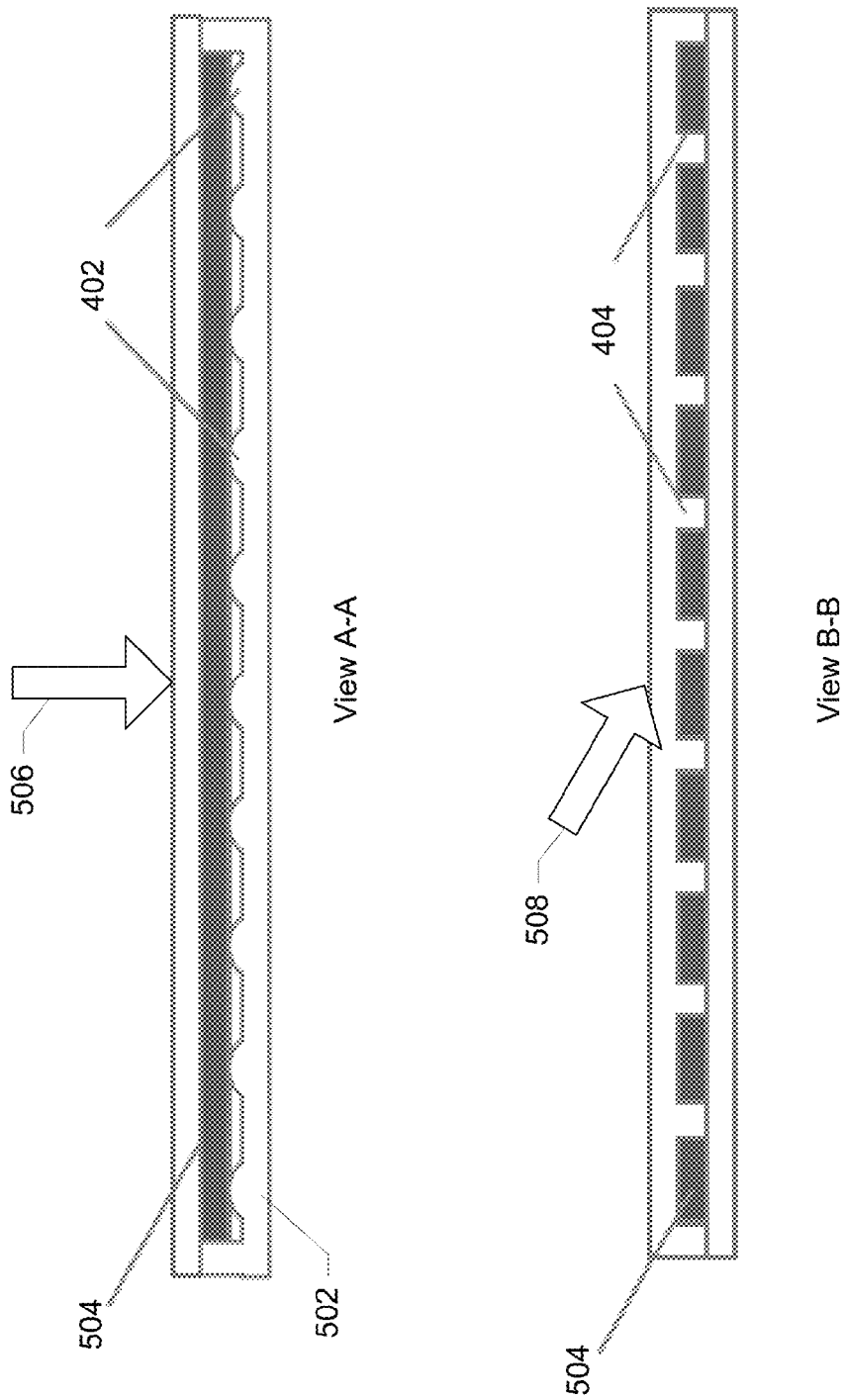
FIG. 5 includes cross-sectional views of two-dimensional sensor arrays.

According to a particular implementation and as illustrated in cross-sectional view A-A of FIG. 5, bumps 402 may be convex features that are formed on or part of a molded silicone sheet 502 that is aligned with and laminated to piezoresistive material 504. In some cases, silicone sheet 502 may form part of an enclosure that provides environmental protection to the enclosed components. In the depicted implementation, bumps 402 are on the side of material away from the conductive traces and are aligned with the array's quantized touch points (e.g., TP-1 through TP-10 of FIG. 2), acting to focus force 506 applied to the top of the array to those touch points. Alternatively, bumps 402 may be formed on some other type of substrate (e.g., a rigid substrate like a printed circuit board). Bumps may also be formed in the piezoresistive material itself by shaping of the material at the desired locations. This may be accomplished by, for example, forming the bumps into the fabric when it is made or by embossing the features into the fabric. In another alternative, the bumps may be formed on a backing sheet to which the piezoresistive material is secured (e.g., laminated). Other variations apparent to those of skill in the art are within the scope of this disclosure. In addition, a wide variation in quantization and response (e.g., dynamic range) may be achieved by varying the size, height, spacing and flexibility of bumps 402.

Posts 404 extend through piezoresistive material 504 as shown in cross section view B-B of FIG. 5 and may serve multiple purposes. For example, posts 404 may serve to keep the array components aligned. This may be particularly important where posts 404 are used in conjunction with bumps 402 as shown in region 412 of FIG. 4. Not only would such an arrangement serve to maintain alignment of bumps 402 with the desired quantized touch points, posts 404 may also serve to promote quantization by deflecting force laterally toward adjacent bumps 402. In addition, the substrate from which posts 404 extend may form part of an enclosure that provides environmental protection to the enclosed components.

According to some implementations, posts 404 may not extend all of the way through piezoresistive material 504 (i.e., being only secured to one of the substrates on either side of material 504). This would mitigate the scenario in which a touch event occurs directly over a post. In such a scenario, if the post is rigid and extended all the way through the piezoresistive material, the touch event might not register. By contrast, if the post extended only part of the way through the piezoresistive material, a touch event over the post would result in some deflection that would transfer force to the piezoresistive material.

As an alternative and as depicted in FIG. 5, posts 404 may extend all of the way through piezoresistive material 504. In such implementations, posts 404 may be constructed from a flexible material (e.g., silicone) so they compress with touch events. Posts 404 might also be secured to both substrates on either side of the piezoresistive material. Such a configuration might be important, for example, in applications in which lateral shearing forces (e.g., force 508) are expected on the surface of the array. In such applications, securing of the posts in this way would ensure that alignment is maintained in the presence of such shearing forces. Posts 404 may also be tapered to promote some level of compression. More generally, the geometry (taper, thickness, etc.), flexibility, and spacing of posts 404 may be controlled to achieve a desired array response.

Cutouts 406 may be introduced in the piezoresistive material to promote isolation and inhibit cross-talk between conductive traces. This will improve the signal-to-noise ratio for the signals being read from the vertical traces and thereby improve overall system performance. And as will be appreciated, this may also serve to promote the quantization of touch point locations. And some implementations may take advantage of the absence of the piezoresistive material at the cutouts by including posts that are aligned with the cutouts. These may be like posts 404 or may conform more closely to the shape of the cutout. For example, the posts could fill the cutout. As will be appreciated, such an approach would serve to provide mechanical structure, promote alignment, and/or promote a desired dynamic range.

As mentioned above, implementations enabled by this disclosure may be suitable for a broad range of applications. That is, two-dimensional sensor arrays as described herein may be useful in any context in which it is important or desirable to monitor the locations and magnitudes of forces on a surface at a point in time or over a period of time. In one example, such a two-dimensional array might be integrated in athletic footwear to monitor technique or track stress. In another example, a yoga mat might include such a two-dimensional array for the purpose of monitoring and/or teaching proper technique. In another example, the floor of an elder-care facility might include such arrays to indicate that a patient has fallen. In yet another example, an array might be integrated in the seat of an office chair to promote ergonomically sound posture. In still another example, a two-dimensional array might be incorporated in a mattress or pad for use in an infant's crib or bassinet. Such an array would be useful for monitoring an infant's sleeping position and to trigger an alarm when, for example, the sleeping position is determined to represent a high risk for sudden infant death syndrome (SIDS). As will be understood from the diversity of these examples, the potential applications of two-dimensional sensor arrays implemented as described herein are virtually limitless.

It will be understood by those skilled in the art that changes in the form and details of the implementations described herein may be made without departing from the scope of this disclosure. In addition, although various advantages, aspects, and objects have been described with reference to various implementations, the scope of this disclosure should not be limited by reference to such advantages, aspects, and objects. Rather, the scope of this disclosure should be determined with reference to the appended claims.

What is claimed is:
1. A sensor array, comprising:
a piezoresistive substrate;
a first array of conductive traces formed on the piezoresistive substrate and aligned with a first dimension of the sensor array, the conductive traces of the first array being characterized by a first conductivity;
a second array of conductive traces formed on the piezoresistive substrate and aligned with a second dimension of the sensor array, the conductive traces of the second array being characterized by a second conductivity higher than the first conductivity; and
circuitry configured to apply drive signals to the first array of conductive traces, to receive detection signals from the second array of conductive traces, and to determine one or more locations of one or more corresponding touch events on a surface of the sensor array using the drive and detection signals, wherein the circuitry is further configured to drive one end of a first conductive trace of the first array with a first signal, and to drive an opposing end of the first conductive trace with a second signal, the circuitry being further configured to receive a mixed signal from a second conductive trace of the second array, the mixed signal including contributions from the first and second signals via the piezoresistive substrate, the circuitry being further configured to determine a first location of a first touch event along the first conductive trace with reference to a first value representing the contributions of the first and second signals to the mixed signal.

2. The sensor array of claim 1, wherein the piezoresistive substrate comprises a flexible piezoresistive material.

3. The sensor array of claim 1, wherein the first and second arrays of conductive traces are formed on only one side of the piezoresistive substrate, or on both sides of the piezoresistive substrate.

4. The sensor array of claim 1, wherein the conductive traces of the first array are substantially parallel to each other and oriented along the first dimension, and wherein the conductive traces of the second array are substantially parallel to each other and oriented along the second dimension, the first and second dimensions being substantially perpendicular to each other.

5. The sensor array of claim 1, wherein the circuitry is further configured to determine one or more additional locations of one or more additional touch events along any of the conductive traces of the first array that are substantially simultaneous with the first touch event with reference to one or more additional values representing one or more additional mixed signals received from one or more of the conductive traces of the second array.

6. The sensor array of claim 1, wherein the circuitry is further configured to determine the first location of the first touch event as being along the first conductive trace and between adjacent conductive traces of the second array.

7. The sensor array of claim 6, wherein the circuitry is configured to determine the first location of the first touch event with reference to an additional value representing an additional mixed signal received from an additional conductive trace of the second array.

8. The sensor array of claim 1, wherein the circuitry is further configured to determine a second location of second touch event along the first conductive trace that is substantially simultaneous with the first touch event with reference to the first value and an additional value representing an additional mixed signal received from an additional conductive trace of the second array.

9. The sensor array of claim 1, wherein the circuitry is further configured to drive one end of a third conductive trace of the first array with the first signal, and to drive an opposing end of the third conductive trace with a third signal, wherein the mixed signal also includes additional contributions from the first signal and the third signal corresponding to a second touch event near the third conductive trace that is substantially simultaneous with the first touch event, and wherein the circuitry is further configured to generate the first value with reference to the additional contributions from the first and third signals corresponding to the second touch event.

10. The sensor array of claim 1, wherein the circuitry is configured to resolve the first location of the first touch event to one of a plurality of discrete locations associated with the first conductive trace on the surface of the sensor array.

11. The sensor array of claim 1, wherein the circuitry is further configured to determine a force value for each touch event representing a magnitude of a force for the corresponding touch event.

12. The sensor array of claim 11, wherein the circuitry is configured to determine the force value for each touch event with reference to an amplitude of a corresponding one of the detection signals.

13. The sensor array of claim 1, wherein each of the conductive traces of the first array coincides with each of the conductive traces of the second array, and wherein the circuitry is further configured to generate a data set for the sensor array with reference to the detection signals, the data set including a data value for each coincidence of one of the conductive traces of the first array with one of the conductive traces of the second array, the circuitry being configured to determine the one or more locations of the one or more corresponding touch events with reference to the data set.

14. The sensor array of claim 13, wherein the circuitry is further configured to determine a first location of a first touch event near a first coincidence of a first conductive trace of the first array and a second conductive trace of the second array by comparing the data value corresponding to the first coincidence to a threshold.

15. The sensor array of claim 14, wherein the threshold is determined with reference to an average of the data values.

16. The sensor array of claim 13, wherein the circuitry is configured to repeat generation of the data set resulting in a plurality of data sets, each data set representing a state of the sensor array for a corresponding period of time, the circuitry being configured to determine the one or more locations of the one or more corresponding touch events with reference to the plurality of data sets.

17. The sensor array of claim 16, wherein the circuitry is configured to determine the one or more locations of the one or more corresponding touch events with reference to the plurality of data sets by comparing corresponding data values in successive ones of the data sets.

18. The sensor array of claim 13, wherein the circuitry is configured to generate first and second data values for each coincidence of one of the conductive traces of the first array with one of the conductive traces of the second array, the first data value representing a location of any nearby touch event along the corresponding conductive trace of the first array, and the second data value representing a force associated with the nearby touch event.

19. The sensor array of claim 1, wherein the circuitry is configured to determine a plurality of locations of a plurality of substantially simultaneous touch events on the surface of the sensor array using the drive and detection signals.

20. The sensor array of claim 1, wherein the circuitry is configured to resolve detected touch events to a plurality of discrete locations on the surface of the sensor array.

21. The sensor array of claim 20, further comprising a plurality of force focusing elements, each force focusing element being aligned with one of the discrete locations.

22. The sensor array of claim 21, wherein the force focusing elements are part of the piezoresistive substrate.

23. The sensor array of claim 21, further comprising an additional substrate adjacent to a combination of the first and second arrays of conductive traces and the piezoresistive substrate, the additional substrate having the force focusing elements formed thereon.

24. The sensor array of claim 23, wherein the force focusing elements comprises convex features on the additional substrate.

25. The sensor array of claim 23, wherein the additional substrate is part of an environmental protection enclosure for the combination of the first and second arrays of conductive traces and the piezoresistive substrate.

26. The sensor array of claim 21, wherein one or both of a form factor of the force focusing elements and a flexibility of the force focusing elements is controlled to achieve a corresponding dynamic range of the sensor array.

27. The sensor array of claim 1, further comprising a first additional substrate adjacent to a combination of the first and second arrays of conductive traces and the piezoresistive substrate, the first additional substrate having a plurality of structural elements extending therefrom at least partially through the piezoresistive substrate in spaces between the conductive traces, the sensor array further comprising a second additional substrate adjacent to the combination of the first and second arrays of conductive traces and the piezoresistive substrate on an opposite side of the combination from the first additional substrate.

28. The sensor array of claim 27, wherein the structural elements extend all of the way through the piezoresistive substrate and contact the second additional substrate without force exerted on the surface of the sensor array.

29. The sensor array of claim 27, wherein the structural elements extend only part of the way through the piezoresistive substrate.

30. The sensor array of claim 27, wherein the first and second additional substrates are part of an environmental protection enclosure for the combination of the first and second arrays of conductive traces and the piezoresistive substrate.

31. The sensor array of claim 1, wherein the piezoresistive substrate includes a plurality of apertures, each of the apertures being aligned with a space between the conductive traces of the first and second arrays.

32. The sensor array of claim 31, further comprising an additional substrate adjacent to a combination of the first and second arrays of conductive traces and the piezoresistive substrate, the additional substrate having a plurality of structural elements extending therefrom at least partially through the apertures of the piezoresistive substrate.

33. The sensor array of claim 32, wherein the structural elements have a form factor corresponding to a shape of the apertures.

34. The sensor array of claim 1, wherein the conductive traces of the first array are resistive traces, and wherein the circuitry is configured to energize each of the conductive traces of the first array by simultaneously driving opposing ends of the conductive trace with first and second signals, respectively, using a plurality of signal busses, each signal buss being connected to a plurality of the conductive traces of the first array, the opposing ends of each conductive trace of the first array being connected to a unique pair of the busses.

35. The sensor array of claim 34, wherein the conductive traces of the second array are characterized by substantially zero resistance, and wherein at least some of the locations at which the circuitry is configured to determine touch events are along corresponding ones of the conductive traces of the first array and between respective pairs of the conductive traces of the second array.

36. The sensor array of claim 1, wherein the circuitry is configured to resolve detected touch events to a plurality of discrete locations on the surface of the sensor array, the plurality of discrete locations forming an array of Y discrete locations along the first dimension by X discrete locations along the second dimension, the first array of conductive traces including X conductive traces, and the second array of conductive traces including fewer than Y conductive traces, where X and Y are integers greater than zero.

37. The sensor array of claim 1, wherein the circuitry is configured to resolve detected touch events to a plurality of discrete locations on the surface of the sensor array, the plurality of discrete locations forming an array of Y discrete locations along the first dimension by X discrete locations along the second dimension, the first array of conductive traces including X conductive traces, where X and Y are integers greater than zero, the sensor array further comprising a plurality of busses by which the circuitry applies the drive signals to the first array of conductive traces, the plurality of busses including fewer than X busses.

38. The sensor array of claim 1, wherein each of the conductive traces of the first array coincides with each of the conductive traces of the second array, the sensor array further comprising a trace pattern at each coincidence of one of the conductive traces of the first array with one of the conductive traces of the second array, each trace pattern including a first trace extending from the corresponding conductive trace of the first array and a second trace extending from the corresponding conductive trace of the second array, the first and second traces having complementary shapes.

39. The sensor array of claim 38, wherein the complementary shapes of the first and second traces of each trace pattern comprise a clover shape and a cruciform shape.

40. The sensor array of claim 38, wherein one or both of the shapes of the first and second traces and the distance between the first and second traces is controlled to achieve a corresponding dynamic range of the sensor array.

41. A sensor array, comprising:
a first array of conductive traces aligned with a first dimension of the sensor array, the conductive traces of the first array characterized by a first conductivity;
a second array of conductive traces aligned with a second dimension of the sensor array, the conductive traces of the second array characterized by a second conductivity higher than the first conductivity;
piezoresistive material configured to provide electrical connectivity between the conductive traces of the first and second arrays; and
circuitry configured to apply drive signals to the first array of conductive traces, to receive detection signals from the second array of conductive traces, and to determine one or more locations of one or more corresponding touch events on a surface of the sensor array using the drive and detection signals, the circuitry being further configured to drive one end of a first conductive trace of the first array with a first signal, and to drive an opposing end of the first conductive trace with a second signal, the circuitry being further configured to receive a mixed signal from a second conductive trace of the second array, the mixed signal including contributions from the first and second signals via the piezoresistive material, the circuitry being further configured to determine a first location of a first touch event along the first conductive trace with reference to a first value representing the contributions of the first and second signals to the mixed signal.

42. The sensor array of claim 41, wherein the circuitry is further configured to determine one or more additional locations of one or more additional touch events along any of the conductive traces of the first array that are substantially simultaneous with the first touch event with reference to one or more additional values representing one or more additional mixed signals received from one or more of the conductive traces of the second array.

43. The sensor array of claim 41, wherein the circuitry is further configured to determine the first location of the first touch event as being along the first conductive trace and between adjacent conductive traces of the second array.

44. The sensor array of claim 43, wherein the circuitry is configured to determine the first location of the first touch event with reference to an additional value representing an additional mixed signal received from an additional conductive trace of the second array.

45. The sensor array of claim 41, wherein the circuitry is further configured to determine a second location of second touch event along the first conductive trace that is substantially simultaneous with the first touch event with reference to the first value and an additional value representing an additional mixed signal received from an additional conductive trace of the second array.

46. The sensor array of claim 41, wherein the circuitry is further configured to drive one end of a third conductive trace of the first array with the first signal, and to drive an opposing end of the third conductive trace with a third signal, wherein the mixed signal also includes additional contributions from the first signal and the third signal corresponding to a second touch event near the third conductive trace that is substantially simultaneous with the first touch event, and wherein the circuitry is further configured to generate the first value with reference to the additional contributions from the first and third signals corresponding to the second touch event.

47. The sensor array of claim 41, wherein the circuitry is configured to resolve the first location of the first touch event to one of a plurality of discrete locations associated with the first conductive trace on the surface of the sensor array.

48. The sensor array of claim 41, wherein the conductive traces of the first array are resistive traces, and wherein the circuitry is configured to energize each of the conductive traces of the first array by simultaneously driving opposing ends of the conductive trace with first and second signals, respectively, using a plurality of signal busses, each signal buss being connected to a plurality of the conductive traces of the first array, the opposing ends of each conductive trace of the first array being connected to a unique pair of the busses.

49. The sensor array of claim 48, wherein the conductive traces of the second array are characterized by substantially zero resistance, and wherein at least some of the locations at which the circuitry is configured to determine touch events are along corresponding ones of the conductive traces of the first array and between respective pairs of the conductive traces of the second array.

50. The sensor array of claim 41, wherein the circuitry is configured to resolve detected touch events to a plurality of discrete locations on the surface of the sensor array, the plurality of discrete locations forming an array of Y discrete locations along the first dimension by X discrete locations along the second dimension, the first array of conductive traces including X conductive traces, and the second array of conductive traces including fewer than Y conductive traces, where X and Y are integers greater than zero.

51. The sensor array of claim 41, wherein circuitry is configured to resolve detected touch events to a plurality of discrete locations on the surface of the sensor array, the plurality of discrete locations forming an array of Y discrete locations along the first dimension by X discrete locations along the second dimension, the first array of conductive traces including X conductive traces, where X and Y are integers greater than zero, the sensor array further comprising a plurality of busses by which the circuitry applies the drive signals to the first array of conductive traces, the plurality of busses including fewer than X busses.

52. The sensor array of claim 41, wherein the piezoresistive material comprises a flexible piezoresistive substrate.

53. The sensor array of claim 52, wherein the first and second arrays of conductive traces are formed on the flexible piezoresistive substrate.

54. The sensor array of claim 53, wherein the first and second arrays of conductive traces are formed on only one side of the flexible piezoresistive substrate, or on both sides of the flexible piezoresistive substrate.

55. The sensor array of claim 41, wherein one or both of the first and second arrays of conductive traces are formed on one or more additional substrates adjacent to the flexible piezoresistive substrate.

* * * * *